United States Patent [19]

Crowninshield

[11] Patent Number: 4,718,912
[45] Date of Patent: Jan. 12, 1988

[54] FEMORAL COMPONENT AND THE METHOD OF CONSTRUCTING THE SAME

[75] Inventor: Roy D. Crowninshield, Warsaw, Ind.
[73] Assignee: Zimmer Inc., Warsaw, Ind.
[21] Appl. No.: 796,684
[22] Filed: Nov. 12, 1985
[51] Int. Cl.$^4$ .............................. A61F 2/36; A61F 2/32
[52] U.S. Cl. ........................................... 623/23; 623/22
[58] Field of Search ............................. 623/23, 22, 16; 128/92 YO, 92 X

[56] References Cited

U.S. PATENT DOCUMENTS 4,589,883 5/1986 Kenna ................................... 623/22
4,608,053 8/1986 Keller ................................... 623/23

FOREIGN PATENT DOCUMENTS 3001521 4/1981 Fed. Rep. of Germany ........ 623/16

OTHER PUBLICATIONS

Intermedics Orthopedics Ad, JBJS, vol. 66-A, Dec. 9, 1984, Zimmer Ad, The Total System ©1984.
Depuy Ad, AML Total Hip System with Porocoat, JBJS, 66-B5, Nov. 1984, Biomed. AD PSN-28 Hip System, undated.
Osteonics Ad, HS2P Micro Structured Hip System, undated, Howmedica Ad, PCA TM Total Hip System JBJS No. 66-A, Oct. 8, 1984.
Osteonics Ad, Integrated Systems of Implants, Let No. PF4, undated.

Primary Examiner—Richard J. Apley
Assistant Examiner—Alan W. Cannon
Attorney, Agent, or Firm—Paul David Schoenle

[57] ABSTRACT

A femoral component for a hip prosthesis includes a stem with a porous surface or the like to enhance bone fixation. The porous surface is applied to the stem in a predetermined manner to accommodate stress lines for the stem and generate a curvilinear inferior boundary for the porous surface. A method of construction utilizes the stress lines to approximate a boundary for the porous surface.

7 Claims, 4 Drawing Figures

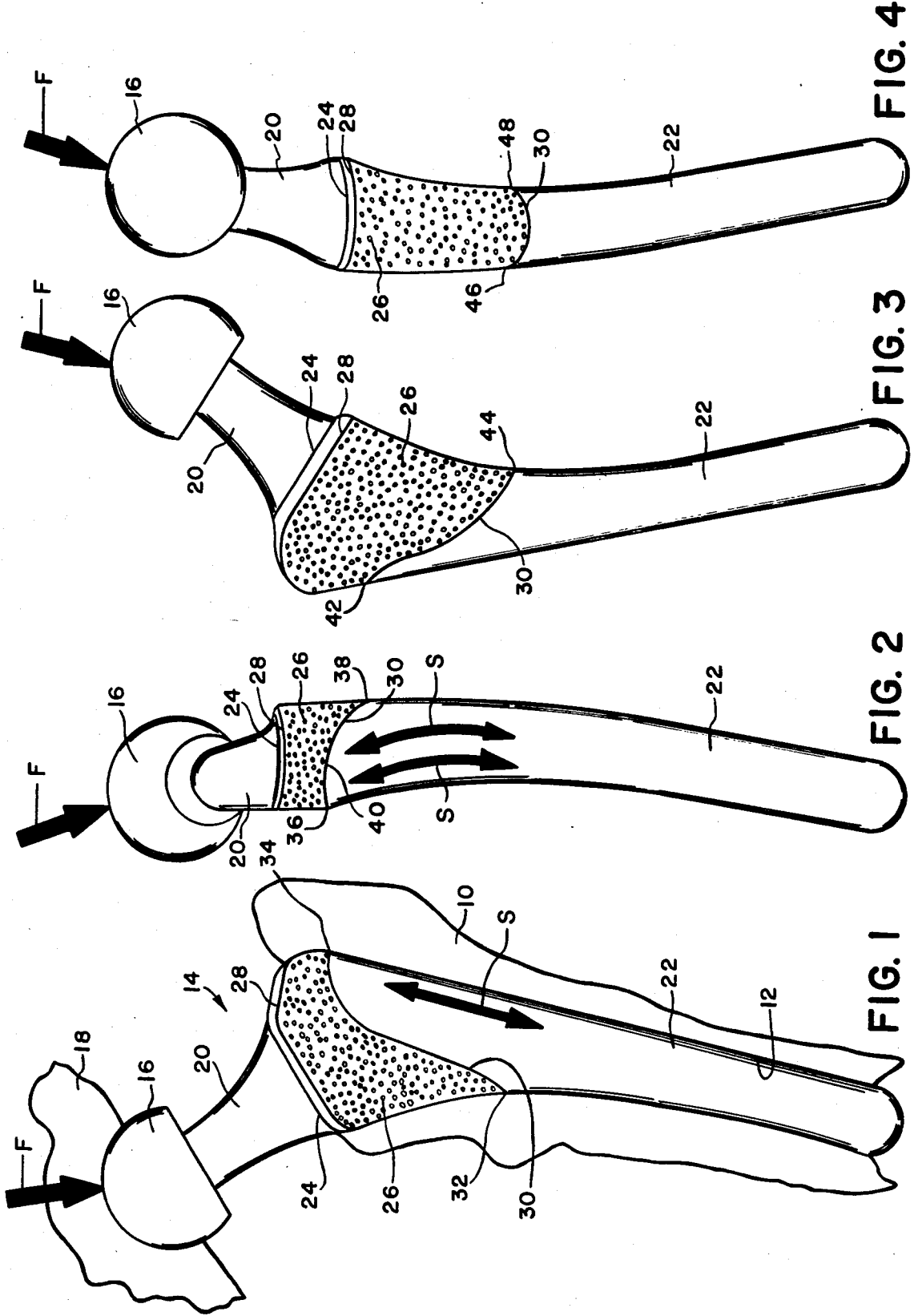

FEMORAL COMPONENT AND THE METHOD OF CONSTRUCTING THE SAME

The present invention relates to a femoral component for a hip prosthesis wherein the head of a femur is resected to accommodate a stem of the femoral component. Such a procedure is commonly referred to as a hip replacement.

Heretofore, the fixation of the stem of the femur was provided by a cement mixture which rigidly secured the stem within an intramedullary canal of a femur that had its femoral head resected. As an alternative it has been the practice more recently to provide a porous surface or precoat of cement to the stem so that, in the first case, bony ingrowth could permeate the porous surface for fixation thereto, or, in the second case, cement could securely adhere to the precoated stem. In all of these cases the portion of the stem receiving the precoat or the porous surface has been provided with substantially symmetrical surfaces on the anterior side and the posterior side. Moreover, when a porous surface was provided for the stem, the stem was notched or suitably recessed to provide a cavity receiving the porous surface. The notching on the stem generated areas where stress would concentrate to limit the maximum load which could be applied to the stem.

The present invention accommodates the stress experienced by a femoral component to define a "stress-dependent" contour for the stem so that a porous coating is applied to the stem at locations of low stress. In particular, the present invention provides a stem with a porous coating that defines a boundary that is asymmetrical to account for the different stress experienced by an anterior side of the stem and a posterior side of the stem.

It is an object of the present invention to provide a femoral component with a stem of high functional strength by avoiding surface irregularities at the location of highest stress while at the same time providing a porous surface for the stem.

In FIG. 1 a (front) anterior view femoral component is shown in the desired position within a femur following hip replacement surgery.

FIG. 2 is a right side view of the femoral component only of FIG. 1.

FIG. 3 is a rear view of the femoral component only of FIG. 1.

FIG. 4 is a left side view of the femoral component only of FIG. 1.

During hip replacement surgery a femoral head (not shown) for a femur 10 is resected and an intramedullary canal 12 is reamed open so that a femoral component 14 can fit within the canal 12. The femoral component 14 includes a ball 16 at the proximal end which is spherical to cooperate with an acetabulum 18 or a prosthetic acetabular cup. A neck 20 connects the ball 16 with a stem 22 and a ridge 24 is defined at the intersection of the neck 20 and the stem 22. In order to provide for bony ingrowth, a porous surface 26 is provided on the stem adjacent the ridge 24. The present invention is not limited to one type of porous surface, but includes all possible porous surfaces that provide for bony ingrowth as well as other variations such as precoated stems where the stem is modified to accommodate enhanced fixation. The porous surface 26 defines a superior boundary 28 adjacent the ridge 24 and an inferior boundary 30 that defines a predetermined contour as described hereinafter.

In FIG. 1 the anterior side of the stem 22 shows the inferior boundary 30 extending from a distal position 32 at the medial edge to a proximal position 34 at the lateral edge. The contour of the inferior boundary 30 on the anterior side is substantially concave with a curvilinear direction from position 32 to position 34. In particular, the inferior boundary 30 is slightly convex adjacent the distal position 32 and concave over a greater length adjacent the proximal position 34. In FIG. 2, the lateral side of the stem 22 shows the inferior boundary 30 extending from a proximal position 36 at the anterior edge to a distal position 38 at the posterior edge. From the position 36 the inferior boundary extends substantially in a transverse direction to about a midpoint 40 on the lateral side whereupon the inferior boundary 30 arcuately extends distally to position 38. In FIG. 3 the posterior side of the stem shows the inferior boundary 30 extending from a proximal position 42 to a distal position 44. The inferior boundary 30 is substantially convex on the posterior side in FIG. 3 so that the porous surface 26 on the posterior side defines a larger area for bony ingrowth than for the porous surface 26 on the anterior side in FIG. 1. Finally, the medial side of the stem 22 in FIG. 4 shows the inferior boundary 30 extending from a position 46 on the posterior edge to a position 48 on the anterior edge so that a convex contour for the boundary on the medial side locates positions 46 and 48 at substantially the same longitudinal location from the ridge 24.

In order to form the contour for the inferior boundary 30, the femoral component is subjected to a stress analysis by loading the ball 16 with a force F, of magnitude and direction characteristic of the predominent load present on the prosthesis during function, so that the direction and magnitude of stresses S can be identified on the stem. This process is feasible with a finite element analysis or with experimentation by applying strain gauges therefore to the stem. If a maximum stress is set as a function of the fatigue endurance stress for the constituent material, for example at 30,000 psi tensile stress for porous coated titanium alloy, it is possible to plot this maximum on the stress lines to approximate the inferior boundary 30. Consequently, the porous surface 26 will be applied to the stem at a location adjacent the ridge 28 and spaced from that portion of the stem subjected to a tensile stress equal to or greater than 30,000 psi. For other materials the maximum stress will be different than 30,000 psi.

By applying this stress analysis, it is found that the highest stress is experienced at identifiable locations on the anterior and lateral sides so that this portion of the stem should not be modified or notched to accommodate the porous surface 26. Whereas the posterior and medial side can accommodate a larger surface area for the porous surface 26, as shown in FIG. 3 and FIG. 4, to generate the curvilinear inferior boundary 30 surrounding the stem. In the alternative, the inferior boundary 30 could be formed by a series of linear edges for the porous surface 26 in order to approximate the curvilinear contour shown for boundary 30.

I claim:

1. A femoral component for a hip prosthesis comprising a stem cooperating with a femur via a porous surface, the stem including a neck at one end and the porous surface being attached to the stem adjacent the neck such that a superior boundary for the porous surface is adjacent the neck, the porous surface including an inferior boundary with a predetermined contour which is substantially asymmetrical from an anterior side to a posterior side, and the inferior boundary cooperates with the superior boundary in order to define an area for the porous surface on the posterior side which is larger than an area for the porous surface on the anterior side, wherein said boundaries and said porous surface extend completely and continuously around said stem.

2. A femoral component for a hip prosthesis comprising a stem with means on the stem for enhancing bone fixation to the stem, the enhancing means covering a portion of the stem and including a superior boundary cooperating with an inferior boundary to define a surface area for the enhancing means on a posterior side of the stem and on an anterior side of the stem, and the enhancing means surface area on the anterior side is smaller than a surface area for the enhancing means on the posterior side, wherein said boundaries and said enhancing means extend completely and continuously around said stem.

3. A method for constructing a femoral component comprising the steps of providing a stem suitable for disposition in a femoral canal, generating a stress analysis for the stem to define a stem boundary dependent upon a predetermined stress limit for the stem and applying a porous surface to the stem so that an inferior boundary for the porous surface substantially coincides with the stem boundary.

4. The method of claim 3 in which the step of applying a porous surface generates a curvilinear boundary therefore surrounding the stem in the absence of abrupt changes in direction.

5. A femoral component for a hip prosthesis comprising a stem subjected to loads when cooperating with a femur, the stem including a porous surface to enhance fixation between the stem and the femur, and the porous surface on an anterior side of the stem defining an area which is smaller than an area defined by the porous surface on the posterior side in order to reduce the amount of the porous surface on the anterior side which is subjected to the higher loads applied to the stem wherein the porous surface defines a superior boundary and an inferior boundary which both extend completely around the stem, the superior boundary being substantially disposed adjacent a neck which is adapted to support a ball and the inferior boundary defining a smooth transitional curvilinear contour which is asymmetrical from an anterior side to a posterior side.

6. A femoral component for a hip prosthesis comprising a stem subjected to loads when cooperating with a femur, the stem including a porous surface to enhance fixation between the stem and the femur, the porous surface on an anterior side of the stem defining an area which is smaller than an area defined by the porous surface on the posterior side in order to reduce the amount of the porous surface on the anterior side which is subjected to the higher loads applied to the stem, the porous surface defining a superior boundary and an inferior boundary which both extend completely around the stem, the superior boundary being substantially disposed adjacent a neck which is adapted to support a ball and the inferior boundary defining a smooth transitional curvilinear contour which is asymmetrical from an anterior side to a posterior side, and in which the smooth transitional curvilinear contour is also asymmetrical from a lateral side to a medial side.

7. A femoral component for a hip prosthesis comprising a stem region and a head region interconnected by a neck region, said stem region coated with a porous surface which extends substantially from the junction of said neck and said stem to an inferior border which is a predetermined, curvilinear, asymmetrical contour that has been determined by stress analysis of said component while axially loading said component in compression, said contour being defined as concave on the lateral face of said stem, convex on the medial face of said stem and transitionally convex to concave on the anterior and posterior faces of said stem when traversing said stem from said medial to said lateral face, such that the area of said porous surface covering said medial face is substantially greater than the area of said porous surface covering said lateral face and the area of said porous surface covering said posterior face is substantially greater than the area of said porous surface covering said anterior face, and said coated anterior surface is substantially asymmetrical to said coated posterior surface, said porous surface being selectively disposed on said stem with said asymmetrical boundary circumventing that portion of the stem subjected to the highest stress.

* * * * *